United States Patent
Betley et al.

(10) Patent No.: US 8,076,477 B2
(45) Date of Patent: Dec. 13, 2011

(54) ADSORBENTS FOR PROTEIN PURIFICATION

(75) Inventors: Jason Richard Betley, Hertfordshire (GB); Helen Tatton, Hampshire (GB); Kelly Le Riche, Berkshire (GB); Matthew Webb, Suffolk (GB)

(73) Assignee: ProMetic BioSciences Ltd., Isle of Man, British Isles (GB)

( * ) Notice: Subject to any disclaimer, the term of this patent is extended or adjusted under 35 U.S.C. 154(b) by 216 days.

(21) Appl. No.: 12/281,346

(22) PCT Filed: Mar. 2, 2007
(Under 37 CFR 1.47)

(86) PCT No.: PCT/GB2007/050095
§ 371 (c)(1),
(2), (4) Date: Mar. 18, 2009

(87) PCT Pub. No.: WO2007/099374
PCT Pub. Date: Sep. 7, 2007

(65) Prior Publication Data
US 2009/0221801 A1      Sep. 3, 2009

(30) Foreign Application Priority Data
Mar. 2, 2006  (GB) .................................. 0604236.0

(51) Int. Cl.
*C07D 251/46* (2006.01)
*C07D 251/52* (2006.01)
*C07D 251/54* (2006.01)
*C07D 251/38* (2006.01)
*C07D 251/30* (2006.01)
*A61K 31/53* (2006.01)
*B01J 20/22* (2006.01)
*G01N 30/00* (2006.01)

(52) U.S. Cl. ........ 544/194; 544/196; 544/204; 544/219; 544/241; 544/245; 436/177; 436/178; 436/161; 436/86; 436/63

(58) Field of Classification Search .................. 544/194, 544/196, 204, 219; 514/241, 245
See application file for complete search history.

(56) References Cited

U.S. PATENT DOCUMENTS 6,117,996 A * 9/2000 Lowe et al. ................... 544/216
2003/0166002 A1 * 9/2003 Chang et al. .................. 435/7.1

FOREIGN PATENT DOCUMENTS

WO         WO 97/10887 A1      3/1997
WO         WO 2004/035199 A1   4/2004

OTHER PUBLICATIONS

Stankova et al., Moelcular Diversity, 2, 75-80, 1996.*
Scharn et al., J. Comb. Chem., 2, 361-369, 2000.*
Filippusson et al. , J. Mol. Recognit. 13:370-381, 2000.*
Palanisamy J. Mol. Recognit. 12: 57-66, 1999.*
Meng et al., "Cleavable Linkers for Porous Silicon-Based Mass Spectrometry," *Angew. Chem. Int. Ed.*, 2004, vol. 43, pp. 1255-1260.

* cited by examiner

*Primary Examiner* — Venkataraman Balasubramanian
(74) *Attorney, Agent, or Firm* — Saliwanchik, Lloyd & Eisenschenk

(57) ABSTRACT

Use of an affinity adsorbent for the separation, removal, isolation, purification, characterisation, identification or quantification of a proteinaceous material, wherein the affinity adsorbent is a compound of formula (III), wherein $R_1$ is H, alkyl, aryl, hydroxyalkyl, cyciohexyl, amino or a heterocyclic group which is optionally substituted with one or more of alkyl, aryl, alkoxy, aryloxy, acyloxy, acylamino, amino, OH, $CO_2H$, sulphonyl, carbamoyl, sulphamoyl, alkylsuiphonyl and halogen; one X is N and the other is N, C—Cl or C—CN; Y is O, S or $NR_2$; Z is O, S or $NR_3$; $R_2$ and $R_3$ are each H, alkyl, hydroxyalkyl, benzyl or β-phenylethyl; Q is benzene, naphthalene, benzthiazole, benzoxazole, 1-phenylpyrazole, indazoie or benzimidazoie; $R_4$, $R_5$ and $R_6$ are each H, OH, alkyl, aryl, heterocyclic, alkoxy, aryloxy, amino, acyloxy, acylamino, $CO_2H$, sulphonic acid, carbamoyl, suiphamoyl, alkylsulphonyl or halogen, or two or more of $R_4$, $R_5$ and $R_6$ are linked to form a cyclic structure; U and V are the same or different $C_{1-10}$ straight-chain alkylene groups optionally substituted by one or more of hydroxyl, alkyl, aryl, hydroxyl, alkyl, β-phenylethyl and halogen; and A is a support matrix optionally linked to the X-containing ring by a spacer.

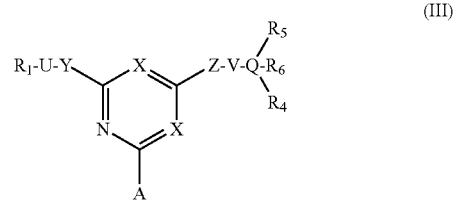

20 Claims, No Drawings

ADSORBENTS FOR PROTEIN PURIFICATION

This application is a National Stage Application of International Application Number PCT/GB2007/050095, filed Mar. 2, 2007; which claims priority to Great Britain Patent Application No. 0604236.0, filed Mar. 2, 2006, all of which are incorporated herein in their entirety.

FIELD OF THE INVENTION

This invention relates to compounds and their use as affinity ligands for protein purification.

BACKGROUND OF THE INVENTION

Antibodies are immunoglobulin glycoproteins having a basic unit of a monomer structure. The monomer is a Y-shaped protein that consists of four polypeptide chains, two of which are identical heavy chains and two are identical light chains connected by disulphide bridges. There are five different types of heavy chain ($\gamma$, $\mu$, $\alpha$, $\epsilon$ and $\delta$) that distinguish the immunoglobulin classes (IgG, IgM, IgA, IgD and IgE, respectively). There are also two different types of light chain ($\lambda$ and $\kappa$) resulting from different gene products.

IgG (a monomeric immunoglobulin approximately of 150 kD in size) provides antibody-based immunity against invading pathogens and, due to the high specificity that IgG has towards specific antigens within the body, it is the most commonly used reagent in immunological research and clinical diagnostics.

Monoclonal antibodies (herein termed Mabs) are antibodies that have identical specificity towards a single antigen and are generated from a cell line that has been produced from a single cloned cell. Mabs constitute the fastest growing sector in the biopharmaceutical industry where is it estimated that sales will reach $30 billion (US) by 2010. Antibody titres from mammalian cell cultures have continued to improve over the last 20 years and alternative downstream processes and chromatography adsorbents are required to resolve the process bottlenecks in the processing of Mabs.

Antibody fragments (parts of whole antibody molecules) offer several advantages over whole antibodies. They are easier and more cost effective to manufacture, they have fewer side-effects in patients, by reducing the risk of cytokine release and its associated toxicity, due to the absence of the Fc (heavy chain) region, and they can be modified to include therapeutic payloads. There are several types of antibody fragments that are either IgG' domains prepared by specific endopeptidase enzyme digestion or that have been genetically engineered in cell lines. These include monovalent fragments such as Fab', Fab and scFv; bivalent fragments such as F(ab')$_2$ diabodies and minibodies; and multivalent fragments such as triabodies and tetrabodies.

Many antibody fragment products are in development for use as therapeutics or in diagnostics. Recombinant antibody fragments are expected to have a significant share of the $6 billion (US) per year diagnostic market, from in vitro immunoassays to in vivo tumour and clot imaging applications (Holliger, P., & Hudson P. J., Nat. Biotech 23 (9; 2005) 1126-1136).

Most antibody fragment products lack a protein A-binding site and therefore, unlike full-chain antibodies, cannot be purified by protein A affinity chromatography. In most instances, conventional chromatography techniques are used to purify antibody fragments. Protein L, a protein with a molecular weight of 35000 Daltons derived from a bacterial species of Peptostreptococcus magnus, is known to bind to antibody light chains and has been investigated for the purification of some antibody fragments but is not considered to be cost-effective and is not available in commercial quantities.

WO97/10887 discloses triazine-based compounds, useful as affinity adsorbents, of formula I

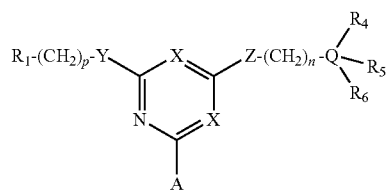

wherein $R_1$ is H, alkyl, hydroxyalkyl, cyclohexyl, $NH_2$, phenyl, naphthyl, 1-phenylpyrazole, indazole, benzthiazole, benzoxazole or benzimidazole, any of which aromatic groups can be substituted with one or more of alkyl, alkoxy, acyloxy, acylamino, amino, $NH_2$, OH, $CO_2H$, sulphonyl, carbamoyl, sulphamoyl, alkylsulphonyl and halogen;

one X is N and the other is N, C—Cl or C—CN;

Y is O, S or $NR_2$;

Z is O, S or $NR_3$;

$R_2$ and $R_3$ are each H, alkyl, hydroxyalkyl, benzyl or $\beta$-phenylethyl;

Q is benzene, naphthalene, benzthiazole, benzoxazole, 1-phenylpyrazole, indazole or benzimidazole;

$R_4$, $R_5$ and $R_6$ are each H, OH, alkyl, alkoxy, amino, $NH_2$, acyloxy, acylamino, $CO_2H$, sulphonic acid, carbamoyl, sulphamoyl, alkylsulphonyl or halogen;

n is 0 to 6;

p is 0 to 20; and

A is a support matrix optionally linked to the X-containing ring by a spacer.

Compounds of formula I are disclosed as having affinity for proteins such as immunoglobulins, insulin. Factor VII or human growth hormone.

Compounds of related structure are disclosed in WO00/67900 and WO03/097112. They have affinity for endotoxins.

Certain triazine-based compounds disclosed in WO97/10887 have affinity for immunoglobulins. An example of a compound showing such affinity is a compound of structure II

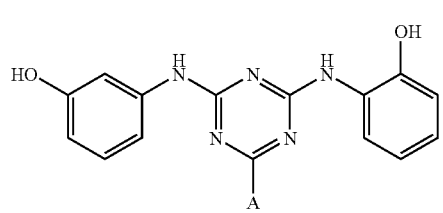

Compounds such as II are able to remove immunoglobulins specifically from complex mixtures or feedstocks such as human plasma.

Another type of commonly encountered feedstock is industrially produced cell culture supernatant, in which monoclonal antibodies are present at concentrations up to 5 g/l of supernatant. Compounds such as II may also be useful for specific removal of monoclonal antibody from these mixtures, although their performance is known to be compromised by the presence of cell culture additives such as Pluronic F-68.

Pluronic F-68 is an anti-foaming agent commonly used in mammalian cell culture. It is a block copolymer of polyoxyethylene and polyoxypropylene, and has a molecular weight of approximately 8000 Da. Pluronic F-68 is used to protect cells from shear and air bubble damage, and is typically used in an amount of 1 g/L in cell culture supernatants. Its presence may reduce or abolish the ability of compounds such as II to remove immunoglobulins from such feedstocks, which represents a considerable obstacle to the use of such ligands for direct capture of monoclonal antibodies from mammalian cell culture media.

SUMMARY OF THE INVENTION

Surprisingly, it has been found that certain compounds, many of which are novel, are useful for affinity-based purification of immunoglobulins, including but not limited to monoclonal antibodies and antibody fragments, even in the presence of compounds such as Pluronic F-68. Compounds for use in the invention are of formula III:

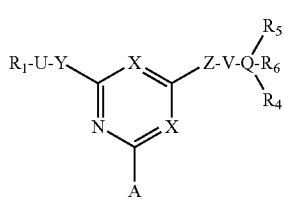

wherein $R_1$ is H, alkyl, aryl, hydroxyalkyl, cyclohexyl, amino or a heterocyclic group, e.g. naphthyl, 1-phenylpyrazole, indazole, benzthiazole, benzoxazole or benzimidazole, any of which aromatic groups may comprise a further fused ring And can be substituted with one or more of alkyl, aryl, alkoxy, aryloxy, acyloxy, acylamino, amino, OH, $CO_2H$, sulphonyl, carbamoyl, sulphamoyl, alkylsulphonyl and halogen;
one X is N and the other is N, C—Cl or C—CN;
Y is O, S or $NR_2$;
Z is O, S or $NR_3$;
$R_2$ and $R_3$ are each H, alkyl, hydroxyalkyl, benzyl or β-phenylethyl;
Q is benzene, naphthalene, benzthiazole, benzoxazole, 1-phenylpyrazole, indazole or benzimidazole;
$R_4$, $R_5$ and $R_6$ are each H, OH, alkyl, aryl, heterocyclic, alkoxy, aryloxy, amino, acyloxy, acylamino, $CO_2H$, sulphonic acid, carbamoyl, sulphamoyl, alkylsulphonyl or halogen, or two or more of $R_4$, $R_5$ and $R_6$ are linked to form a cyclic structure;
U and V are the same or different $C_{1-10}$ straight-chain alkylene groups optionally substituted by one or more of hydroxyl, alkyl, aryl, hydroxyalkyl, β-phenylethyl and halogen such as CHOH; and
A is a support matrix optionally linked to the X-containing ring by a spacer.

Further, compounds of the invention include the corresponding ligands, in which A is replaced by a functional group, linked directly or indirectly to the triazine ring, which can be immobilised on a support matrix. The terms "ligand" and "adsorbent" may be used interchangeably, below.

DESCRIPTION OF THE INVENTION

WO97/10887, WO00/67900 and WO003/097112 disclose how combinatorial libraries of ligands can be built on a solid support. Their disclosures, including examples of embodiments and procedures common to the present invention, are incorporated herein by reference. During the screening of a set of these combinatorial libraries with a feedstock containing albumin, immunoglobulins and Pluronic F-68, a number of ligands were identified as being capable of selectively binding and eluting immunoglobulins.

Compounds of formula III, for use in the invention, can be prepared by procedures known to those skilled in the art. Such procedures are described in the 3 PCT publications identified above; they can be readily adapted to the preparation of new compounds.

In compounds for use in the invention, it is preferred that $R_1$, and/or $QR_4R_5R_6$ is or includes a cyclic structure; either or each cyclic structure preferably has a OH or $SO_3H$ substituent. Preferably, each X is N. Further it is preferred that U and/or V is substituted, e.g. is CHOH. Such substituted compounds are novel.

Preferred immunoglobulin-binding ligands or adsorbents of the invention are of formulae IV-XIII:

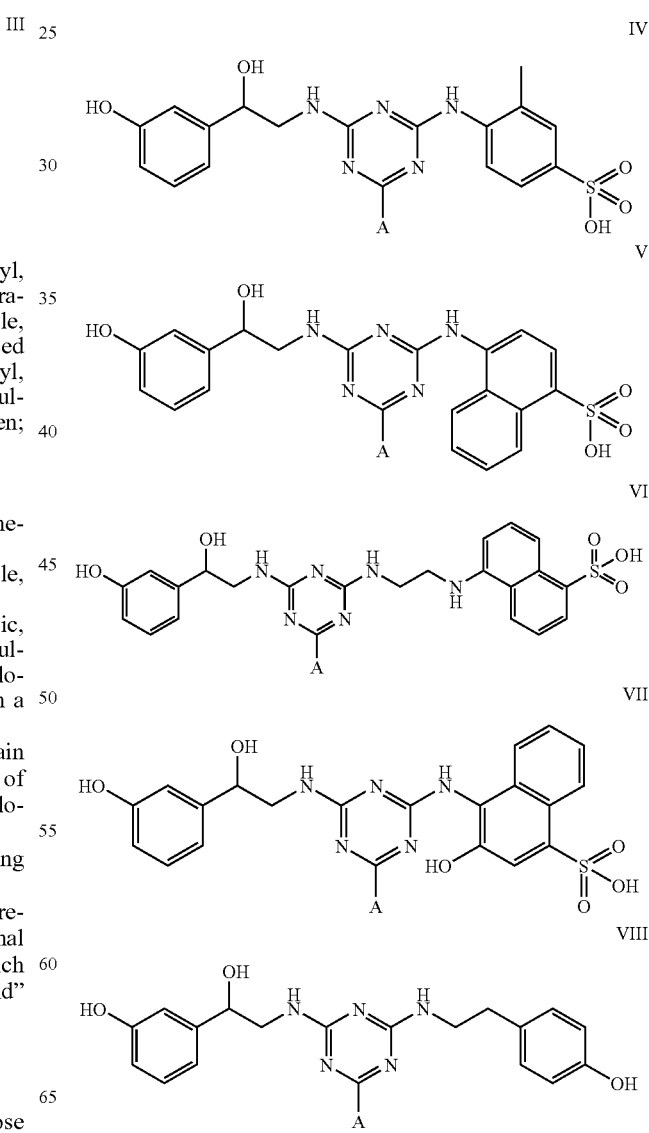

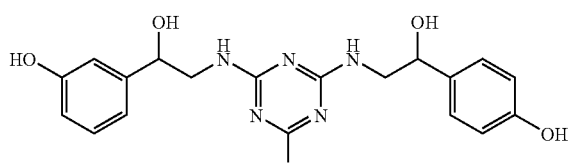

IX

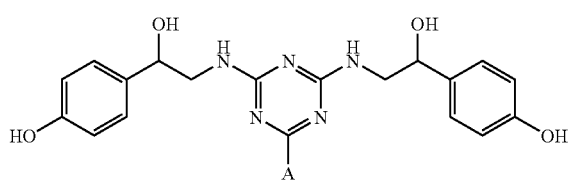

X

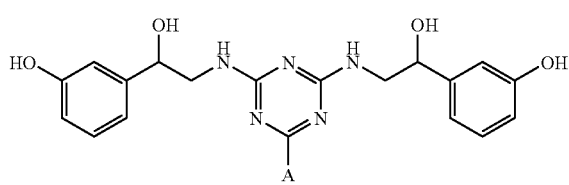

XI

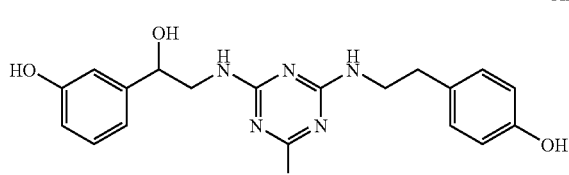

XII

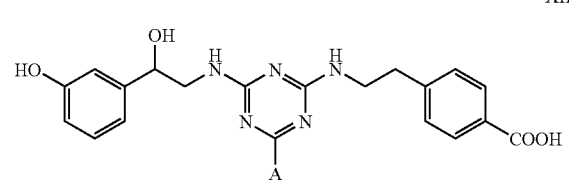

XIII

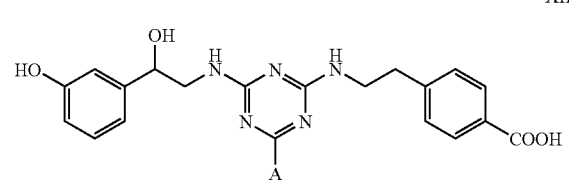

The immunoglobulin-binding ligands described herein are useful for the purification of immunoglobulins from complex mixtures including, but not limited to, human plasma and recombinant fermentation supernatants. This utility is demonstrated below in Example 2, by chromatography experiments using a number of feedstocks.

The term "immunoglobulin" is used herein to describe intact immunoglobulins themselves, including IgG, IgA, IgM and IgE, and also analogues that have the functional or structural characteristics of immunoglobulins, e.g. in terms of affinity to a given compound described herein. Thus, the analyte may be a protein that is a functional fragment of an immunoglobulin, or a structural analogue having one, more or all of the same binding sites, or a fusion protein.

The optional linker may comprise any means of attaching ligands of the invention to support matrices and providing a means of spacing the ligand from the surface of the support matrix. The support matrix may comprise any material, soluble or insoluble, particulate or non-particulate, including fibres and membranes, porous or non-porous. It provides a convenient means of separating ligands of the invention from solutes in a contacting solution. Examples of support matrix and optional linker A include carbohydrate matrices such as agarose, cellulose, dextran, starch, alginate or carrageenan; synthetic polymer matrices such as polystyrene, styrene-divinylbenzene copolymers, polymethacrylates, (e.g. poly(hydroxyethylmethacrylate), polyvinyl alcohol, polyamides or perfluorocarbons; inorganic matrices such as glass, silica or metal oxides; and composite materials.

The following Examples illustrate the invention.

EXAMPLE 1

Synthesis of Adsorbents

The synthesis of adsorbents of the type described is explained in WO97/10887, WO00/67900 and WO03/097112. The synthesis of Adsorbent XI is described and is typical.

6% cross-linked PuraBead agarose gel (650 g settled in RO water) was slurried with RO water (650 mL), 10 M sodium hydroxide (NaOH) (88 mL), and epichlorohydrin (124 mL). The slurry was stirred over 19 hours. Further 10 M sodium hydroxide (NaOH) (22 mL), and epichlorohydrin (37 mL) was then added and the slurry stirred over 1.5 hours. After a sample was taken for analysis, the slurry was filtered then washed with RO water (12×1 L). Analysis for epoxy groups showed that the gel was derivatised with 21.6 µmol epoxy groups per g of settled gel.

The gel was drained before RO water (780 mL) and 0.88 specific gravity ammonia solution (200 mL) were added. The mixture was stirred and heated to 40° C., then stirred at this temperature over 16 hours. After a sample was taken for analysis, the slurry was filtered and then washed with 12×1 L RO water (12×1 L). TNBS analysis for amine groups showed that the gel was derivatised with 20.8 µmol amine groups per g of settled gel.

Settled aminated gel (475 g) was slurried in 1 M potassium phosphate (475 mL) and allowed to settle. 1 M potassium phosphate (140 mL) was then added, the mixture stirred vigorously, and acetone (70 mL) added. The mixture was cooled to 0° C. in an ice salt bath, before cyanuric chloride (11.9 g) in cold acetone (120 mL) was added in one portion. The slurry was stirred over 1 hour at 0-4° C., before being drained, then washed with 50% v/v aqueous acetone (5×500 mL), RO water (5×500 mL), with 50% v/v aqueous acetone (5×500 mL), and RO water (10×500 mL). Analysis revealed the attachment of 25 µmol dichlorotriazine groups per g of settled gel.

The dichlorotriazinyl agarose (50 g) was slurried in RO water (55 mL). Norphenylephrine hydrochloride (1.99 g) was dissolved in RO water (15 mL), 10 M NaOH (0.95 mL) was added, and the mixture was cooled on ice, prior to addition to the dichlorotriazinyl agarose. The mixture was reacted at 60° C. over 19 hours. The gel was washed with 50% DMF (5×100 mL), RO water (5×100 mL), 0.1 M HCl (5×100 mL), 30% IPA/0.2 M NaOH (5×100 mL), RO water (10×100 mL), and 20% aqueous ethanol (3×100 mL) before storage in the cold room in 20% aqueous ethanol.

EXAMPLE 2

Chromatography

Chromatography experiments were performed with each of the adsorbents tabulated in Table 1. For all experiments a 1 cm diameter column was used with a bed height of 5.5 cm and column volume (CV) of 4.3 mL with a linear flow rate of 300 cm/h. The adsorbent was initially equilibrated with 10 CV of phosphate buffered saline (PBS), pH 7.4, and then loaded with pure IgG, IgG feedstock 1 (1 g/L IgG, 1 g/L Pluronic F-68, and other proteins to mimic cell culture supernatant) or 2 (1 g/L IgG, 1 g/L Pluronic F-68 with 5% foetal calf serum), or murine IgG, feedstock up to a concentration of 30 g/L of adsorbent. The adsorbent was then washed with 10 CV of PBS, pH 7.4, before the IgG was eluted with 5 CV of 50 mM citric acid, pH 3.5. The adsorbent then underwent a clean in place (CIP) with 5 CV of 0.5 M sodium hydroxide followed by re-equilibration of the adsorbent with 7 CV of PBS, pH 7.4.

Subsequent to the chromatography experiment, the IgG content of the load, post-load wash, elution and CIP fractions were assessed by nephelometry, A280, HPLC or GPC, to assess the binding and elution capacities and SDS PAGE analysis to assess purity. The binding and elution capacities are summarized in Table 1.

Pure IgG feed contained 1 g/L of polyclonal IgG in PBS, pH 7.4 in the presence or absence of 1 g/L Pluronic F-68. Mock feedstock 1 contained 1 g/L polyclonal IgG, 1 g/L horse skeletal myoglobin, 5 g/L human serum albumin and 1 g/L Pluronic F-68 in CHO cell culture medium. Mock feedstock 2 contained 1 g/L polyclonal IgG, 5% foetal bovine serum and 1 g/L Pluronic F-68 in CHO cell culture medium.

TABLE 1

| Feed | Adsorbent | XI | VI | VII | IV | V | X | IX | VIII |
| --- | --- | --- | --- | --- | --- | --- | --- | --- | --- |
| Pure IgG | Binding Capacity | 3.6 | | | | | 13.3 | 11.2 | 16.4 |
| | Elution Capacity | | | | | | | | 9.1 |
| IgG Feedstock 1 | Binding Capacity | 4.3 | 2.9 | 3.2 | 1.5 | 1.1 | | | 3.75 |
| | Elution Capacity | 2.3 | 0.78* | 2.8 | 0.1 | 0.1 | | | 4.61 |
| IgG Feedstock 2 | Binding Capacity | 5.7 | 3.9 | | | | 3.3 | 7.51 | |
| | Elution Capacity | 3.8 | 0.0 | | | | 0.12 | 0.92 | |
| Murine IgG$_1$ | Binding Capacity | 1.98 | 2.8 | | | | | | |
| | Elution Capacity | 1.1 | 0.0 | | | | | | |

*Elution buffer 50 mM citric acid, pH 3.5 with 30% ethylene glycol and 2 M NaCl.

The chromatographic performance of adsorbent XI was further investigated, to assess the purification capability of the material. Experiments were completed using a 1 cm diameter column with a bed height of 2.5 cm and column volume (CV) of 2.0 mL and a linear flow rate of 50 cm/h (3 minute residence time). The adsorbent was initially equilibrated with 10 CV of phosphate buffered saline (PBS), pH 7.4. 60 mL of IgG$_1$ in a CHO (Chinese Hamster Ovary) cell culture supernatant was loaded onto the column to a concentration of 54 g/L of adsorbent. The adsorbent was then washed with 10 CV of PBS, pH 7.4, before the IgG was eluted with 5 CV of 50 mM sodium citrate at pH 3.0. The adsorbent then underwent a clean in place (CIP) with 5 CV of 0.5 M sodium hydroxide followed by re-equilibration of the adsorbent with 7 CV of PBS, pH 7.4. Fractions (2 mL) were collected throughout the chromatography and analysed for IgG content (Protein A HPLC), DNA content (Picogreen analysis) and total protein (Bradford total protein assay). The breakthrough profile of IgG$_1$ for adsorbent XI shows the binding capacity to be 21.6 g/L and the elution capacity to be 20.9 g/L. Using gel permeation chromatography, the purity of the eluted IgG was determined to be 92.8% and adsorbent XI has a 2 log clearance of DNA.

Chromatography experiments were completed with adsorbent XI using antibody fragments prepared by enzyme (pepsin) digestion. Pepsin is a non-specific endopeptidase that is only active at acid pH and is irreversibly denatured at neutral or alkaline pH. Pepsin digestion results in the generation of one F(ab')$_2$ fragment and several small peptides of the Fc fragment. Fragments of human, ovine and bovine polyclonal antibodies (mixed population of antibodies) were prepared by contacting the IgG with pepsin for 1 hour at 37° C. at pH 4.0. The digestion was halted by adjusting the pH above 7.0, and the F(ab')$_2$ fragments were separated by gel filtration.

The chromatographic performance of adsorbent XI was investigated to assess the purification capability of the material for antibody fragments. Experiments were completed using a 1 cm diameter column with a bed height of 2.5 cm and column volume (CV) of 2.0 mL with a linear flow rate of 50 cm/h (3 minute residence time). The adsorbent was initially equilibrated with 10 CV of phosphate buffered saline (PBS), pH 7.4. Approximately 20 mg of F(ab')$_2$ fragments were loaded per mL of adsorbent. The adsorbent was then washed with 10 CV of PBS, pH 7.4, before the fragments were eluted with 5 CV of 50 mM sodium citrate at pH 3.0. The adsorbent then underwent a clean in place (CIP) with 5 CV of 0.5 M sodium hydroxide followed by re-equilibration of the adsorbent with 7 CV of PBS, pH 7.4. The control for all experiments was Protein L adsorbent (using the same experimental conditions as for adsorbent XI). Each fraction from the chromatography column was collected and analysed using Western blot techniques. This technique indicated that adsorbent XI bound both human kappa and lambda light chain and ovine and bovine F(ab')$_2$ fragments; protein L binds only human kappa light chain and does not bind ovine and bovine fragments.

The invention claimed is:

1. A method for purifying a proteinaceous material, wherein said method comprises contacting a sample containing a proteinaceous material with an affinity adsorbent of formula III

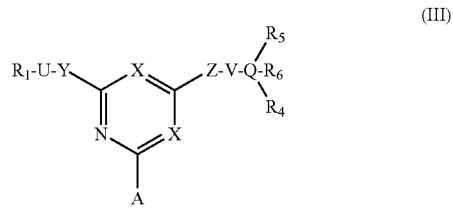

wherein R$_1$ is an aryl or aromatic heterocyclic group which may contain a further fused ring and can be substituted with one or more of alkyl, aryl, alkoxy, aryloxy, acyloxy, acylamino, amino, OH, CO$_2$H, sulphonyl, carbamoyl, sulphamoyl, alkylsulphonyl and halogen;
  X is N;
  Y is O, S or NR$_2$;
  Z is O, S or NR$_3$;
  R$_2$ and R$_3$ are each H, alkyl, hydroxyalkyl, benzyl or β-phenylethyl;
  Q is benzene, naphthalene, benzthiazole, benzoxazole, 1-phenylpyrazole, indazole or benzimidazole;

$R_4$, $R_5$ and $R_6$ are each H, OH, alkyl, aryl, heterocyclic, alkoxy, aryloxy, amino, acyloxy, acylamino, $CO_2H$, sulphonic acid, carbamoyl, sulpharnoyl, alkylsulphonyl or halogen, and $QR_4R_5R_6$ is or includes a cyclic structure;

U and V are the same or different $C_{1-10}$ straight-chain alkylene groups and U and/or V is substituted by OH; and A is a support matrix optionally linked to the X-containing ring by a spacer.

2. The method according to claim 1, wherein either or each cyclic structure has an OH or $SO_3H$ substituent.

3. The method according to claim 1, wherein U and/or V is CHOH.

4. A method for purifying a proteinaceous material, wherein said method comprises contacting a sample containing a proteinaceous material with an affinity adsorbent selected from one of the following:

(IV)
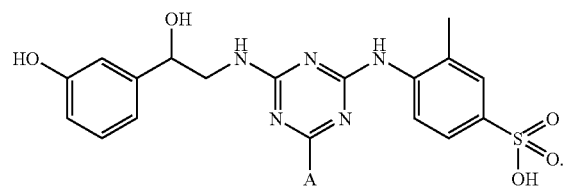

(V)
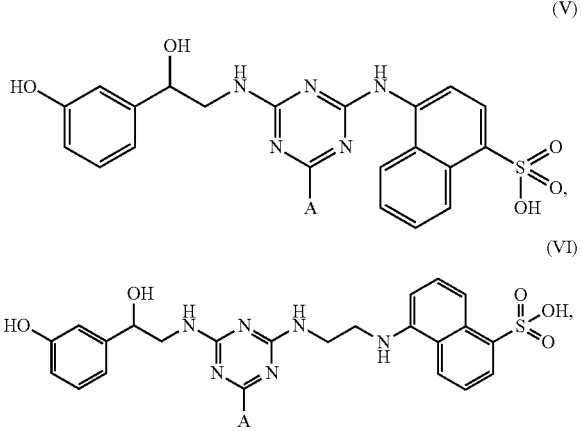

(VI)
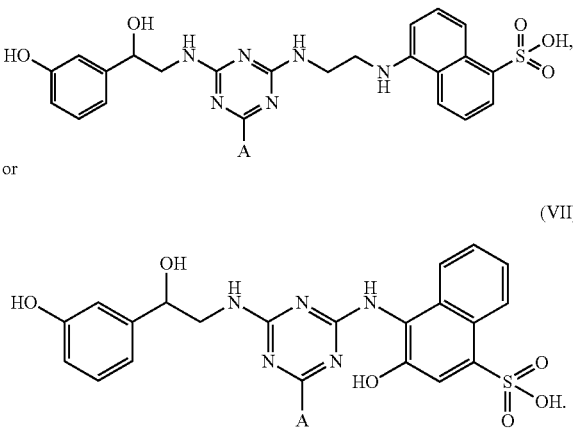

or (VII)
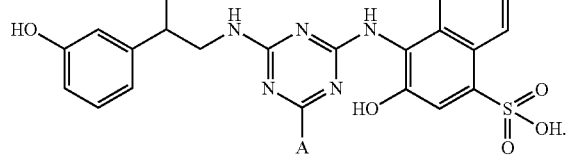

5. The method according to claim 4, wherein the adsorbent is of formula V (V)
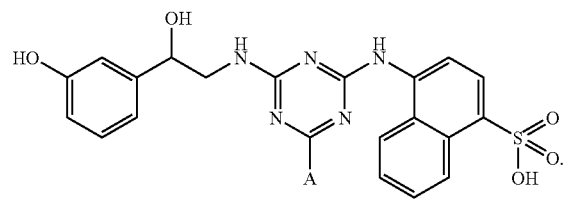

6. The method according to claim 4, wherein the adsorbent is of formula VI (VI)
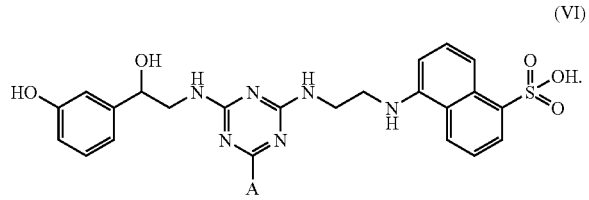

7. The method according to claim 4, wherein the adsorbent is of formula VII (VII)
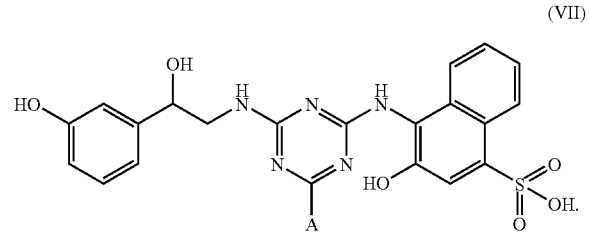

8. The method according to claim 1, wherein the adsorbent is of formula VIII (VIII)
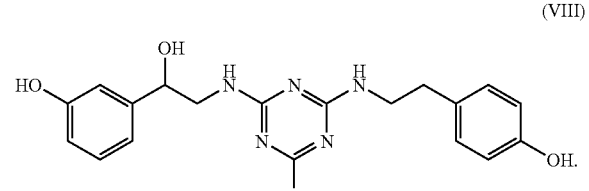

9. The method according to claim 1, wherein the adsorbent is of formula IX (IX)
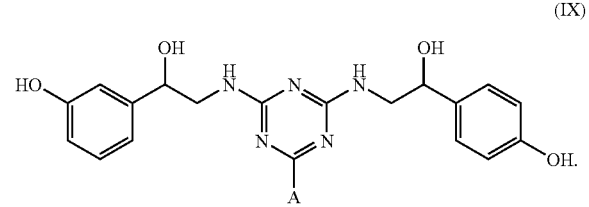

10. The method according to claim 1, wherein the adsorbent is of formula X (X)
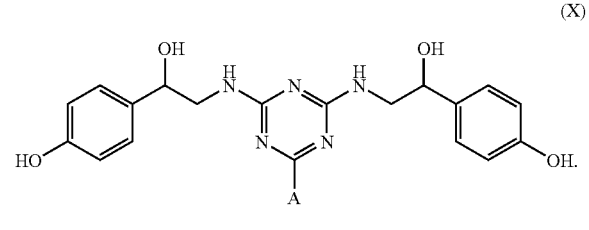

11. The method according to claim 1, wherein the adsorbent is of formula XI

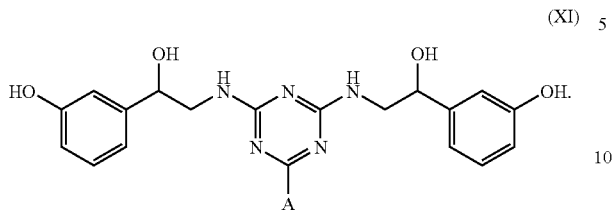

(XI)

12. The method according to claim 1, wherein the proteinaceous material is an immunoglobulin, immunoglobulin fragment or protein.

13. The method according to claim 12, wherein the material is a monoclonal antibody.

14. The method according to claim 12, wherein the material is an immunoglobulin fragment selected from Fab, Fab', F(ab')2, scFV, diabody, minibody, tribody and tetrabody fragments.

15. The method according to claim 1, wherein the proteinaceous material is in cell culture.

16. The method according to claim 1, wherein the proteinaceous material is in combination with an anti-foaming agent.

17. The method according to claim 16, wherein the anti-foaming agent is a block copolymer of polyoxyethylene and polyoxypropylene.

18. A compound of formula III

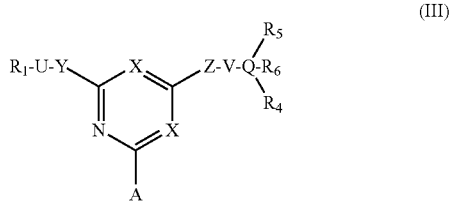

(III)

wherein $R_1$ is an aryl or aromatic heterocyclic group which may contain a further fused ring and can be substituted with one or more of alkyl, aryl, alkoxy, aryloxy, acyloxy, acylamino, amino, OH, $CO_2H$, sulphonyl, carbamoyl, sulphamoyl, alkylsulphonyl and halogen;

X is N;
Y is O, S or $NR_2$;
Z is O, S or $NR_3$;
$R_2$ and $R_3$ are each H, alkyl, hydroxyalkyl, benzyl or β-phenylethy;

Q is benzene, naphthalene, benzthiazole, benzoxazole, 1-phenylpyrazole, indazole or benzimidazole;

$R_4$, $R_5$, and $R_6$ are each H, OH, alkyl, aryl, heterocyclic, alkoxy, aryloxy, amino, acyloxy, acylamino, $CO_2H$, sulphonic acid, carbamoyl, sulphamoyl, alkylsulphonyl or halogen, $QR_4R_5R_6$ is or includes a cyclic structure, and $R_1$ and/or $QR_4R_5R_6$ has an OH or $SO_3H$ substituent;

U and V are the same or different $C_{1-10}$ straight-chain alkylene groups and U and/or V is substituted by OH and A is a support matrix optionally linked to the X-containing ring by a spacer.

19. The compound according to claim 18, wherein U and/or V is CHOH.

20. A method for purifying a proteinaceous material, wherein said method comprises contacting a sample containing a proteinaceous material with an affinity adsorbent of formula III

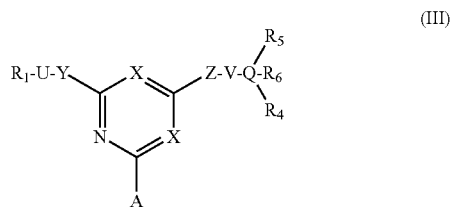

(III)

wherein $R_1$ is an or aromatic heterocyclic group which may contain a further fused ring and can be substituted with one or more of alkyl, aryl, alkoxy, acyloxy, acyloxy, acylamino, amino, OH, $CO_2H$, sulphonyl, carbamoyl, sulphamoyl, alkylsulphonyl and halogen;

X is N;
Y is O, S or $NR_2$;
Z is O, S or $NR_3$;
$R_2$ and $R_3$ are each H, alkyl, hydroxyalkyl, benzyl or β-phenylethyl;

Q is benzene, naphthalene, benzthiazole, benzoxazole, 1-phenylpyrazole, indazole or benzimidazole;

$R_4$, $R_5$ and $R_6$ are each H, OH, alkyl, aryl, heterocyclic, alkoxy, acyloxy, amino, acyloxy, acylamino, $CO_2H$, sulphonic acid, carbamoyl, sulphamoyl, alkylsulphonyl or halogen, and $QR_4R_5R_6$ is or includes a cyclic structure;

U and V are the same or different $C_{1-10}$ straight-chain alkylene groups and U and/or V is substituted by OH; and A is a support matrix optionally linked to the X-containing ring by a spacer, and wherein the proteinaceous material is in combination with an anti-foaming agent.

* * * * *

UNITED STATES PATENT AND TRADEMARK OFFICE
CERTIFICATE OF CORRECTION

| | | |
|---|---|---|
| PATENT NO. | : 8,076,477 B2 | |
| APPLICATION NO. | : 12/281346 | |
| DATED | : December 13, 2011 | |
| INVENTOR(S) | : Jason Richard Betley et al. | |

It is certified that error appears in the above-identified patent and that said Letters Patent is hereby corrected as shown below:

Column 11,
Lines 50 and 51, "β-phenylethy;" should read --β-phenylethyl;--

Column 12,
Line 28, "$R_1$ is an or aromatic" should read --$R_1$ is an aryl or aromatic--
Line 30, "acyloxy, acyloxy" should read --aryloxy, acyloxy--
Line 41, "alkoxy, acyloxy, amino, acyloxy" should read --alkoxy, aryloxy, amino, acyloxy--

Signed and Sealed this
Thirteenth Day of March, 2012

David J. Kappos
*Director of the United States Patent and Trademark Office*